United States Patent [19]
Liu et al.

[11] Patent Number: 5,837,726
[45] Date of Patent: Nov. 17, 1998

[54] ANTIFUNGAL AGENTS DERIVED FROM ASPERGILLUS FUMIGATUS

[75] Inventors: David Qin Liu, Suffern, N.Y.; Zhi-Dong Jiang, Watertown, Mass.; Rex T. Gallagher, Beverly, Mass.; T. Vance Morgan, Natick, Mass.

[73] Assignee: Millennium Pharmaceuticals, Inc., Cambridge, Mass.

[21] Appl. No.: 551,420

[22] Filed: Nov. 1, 1995

[51] Int. Cl.$^6$ .......................... A01N 43/20; C07D 303/00
[52] U.S. Cl. ............................................ 514/475; 549/545
[58] Field of Search .............................. 549/545; 514/475

[56] References Cited

PUBLICATIONS

Kobayashi et al., Isolatin and Structure of an Antifungal Antibiotic, Fusarielin a, and related Compounds Produced by a *Fusarium sp.*, The Journal of Antibiotics, Jan. 1995, pp. 42–52.

*Primary Examiner*—Deborah C. Lambkin
*Attorney, Agent, or Firm*—Fish & Richardson P.C.

[57] ABSTRACT

A natural product of *Aspergillus fumigatus* and specific derivatives thereof, and a method of treating fungal infection therewith.

6 Claims, No Drawings

ANTIFUNGAL AGENTS DERIVED FROM ASPERGILLUS FUMIGATUS

BACKGROUND OF THE INVENTION

Fungal infections (mycoses) may be cutaneous, subcutaneous, or systemic. Superficial mycoses include tinea capitis, tinea corporis, tinea pedis, onychomoycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections also contribute to meningitis and pulmonary or respiratory tract diseases. Opportunistic fungal infections have proliferated, particularly in patients with AIDS.

Like human cells, fungal cells are eukaryotic. Pathogenic organisms include dermatophytes (e.g., *Microsporum canis* and other *M.* spp.; and *Trichophyton* spp. such as *T. rubrum*, and *T. mentagrophytes*), yeasts (e.g., *Candida albicans, C. Tropicalis*, or other *Candida* species), *Torulopsis glabrata, Epidermophyton floccosum, Malassezia furfur* (*Pityropsporon orbiculare*, or *P. ovale*), *Cryptococcus neoformans, Aspergillus fumigatus*, and other *Aspergillus* spp., Zygomycetes (e.g., *Rhizopus, Mucor*), *Paracoccidioides brasiliensis, Blastomyces dermatitides, Histoplasma capsulatum, Coccidioides immitis*, and *Sporothrix schenckii*.

Current antimycotic drugs include nystatin, clotrimazole, amphotericin B, ketoconazole, fluconazole, and itraconazole. *Goodman and Gilman's Pharmacological Basis of Therapeutics,* (8th ed., 1990) Table 44-1, page 1032.

SUMMARY OF THE INVENTION

A natural product having antifungal activity has been isolated and structurally characterized. One aspect of the invention therefore features a substantially pure compound described by the formula (I):

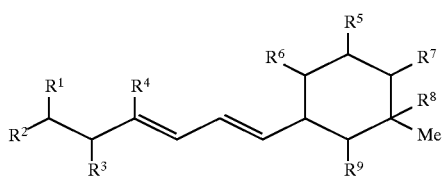

wherein
$R^1$ is $CH_2OH$, $C(O)H$, $C(O)Ac$, $C(O)pBrBz$, $C(O)CH_3$, $C(O)CF_3$, $CO_2CH_3$, $CO_2CF_3C(O)SH$, $C(O)SCH_3$, $C(O)CO_2H$, $C(O)NHR_i$, $C(O)CN$, $C(O)C(O)NH_2$, $CO_2R_{ii}$, $C(O)CH_2C(O)NH_2$, or $C(O)NHCH(R')CO_2Me$, wherein $R_i$ is H, Bn, $C_{1-6}$ alkyl, ($C_{0-6}$ alkyl) ($C_6$ aryl), or $C_{3-6}$ heteroaryl, $R_{ii}$ is H, $C_{1-6}$ alkyl, ($C_{0-6}$ alkyl) ($C_6$ aryl) or $C_{3-6}$ heteroaryl, and R' is H, $C_{1-6}$ alkyl, phenyl, Bn, or $C_{1-6}$ hydroxyalkyl;

$R^2$ is H, $C_{1-6}$ alkyl, ($C_{0-6}$ alkyl)($C_6$ aryl), or $C_{3-6}$ heteroaryl;

$R^3$ is H, Ac, pBrBz, $CH_3$, $CF_3$, F, Cl, Br, I, OH, $OCH_3$, $OCF_3$, $OSi(R_{iii})(R_{iv})(R_v)$, $CO_2R_{vi}$, $SR_{vii}$, $SC(O)R_{viii}$ $SCH_2CH_2SH$, $CO_2H$, $NHR_{ix}$, $NO_2$, CN, $C(O)NH_2$, $CH_2C(O)NH_2$, or $SO_2NH_2$, wherein each of $R_{iii}$, $R_{iv}$, and $R_v$ is independently selected from $C_{1-6}$ alkyl, $R_{vi}$ is $C_{1-6}$ alkyl and each of $R_{vii}$, $R_{viii}$, and $R_{ix}$ is independently selected from H, $C_{1-12}$ alkyl, $C_{6-12}$ aryl, and $C_{3-12}$ heteroaryl); or $R^1$ is —NHC(O)— and $R^3$ is —O—, such that $R^1$ and $R^3$ taken together are a bivalent moiety having the formula (i):

$R^4$ is $C_{1-6}$ alkyl;
$R^5$ is $CH_2C(O)CH_3$ or $CH_2CH(NHR_x)CH_3$, $R_x$ being $C_{1-6}$ alkyl, ($C_{0-6}$ alkyl) ($C_6$ aryl), or $C_{3-6}$ heteroaryl and $R^6$ is —$CH_2CHO$, $CH_2CN$, or $CH_2CO_2H$; or $R^5$ and $R^6$ taken together are a bivalent moiety having one of the formulae (ii) and (iii):

wherein $X_1$ is C or S; $X^2$ is C, N, or O; $R^{10}$ is H, $SR_{xi}$, $NR^aR^b$, $CH_2R^c$, $CH_2CH_2R^d$ or $CH(CH_3)R^e$, wherein $R_{xi}$ is allyl, Bn, $C_{1-12}$ alkyl, $C_{6-12}$ aryl, or $C_{3-12}$ heteroaryl, each of $R^a$, $R^b$, $R^c$ and $R^e$, independently, is H, $C_{1-12}$ alkyl, $C_{6-12}$ aryl, or $C_{3-12}$ heteroaryl, and $R^d$ is $C_{6-12}$ aryl with 0 to 2 halogen substituents or $C_{3-12}$ heteroaryl with 0 to 2 halogen substituents;

$R^{11}$ is $CH_3$ or is absent; $R^{12}$ is H, OH, or is absent;
$R^{13}$ is H, OH, or is absent; or $R^{12}$ and $R^{13}$ taken together are —O—; $R^{14}$ is H, OH, Cl, NHBn, $C(O)R_{xii}$, is absent, or is of the formula (iv):

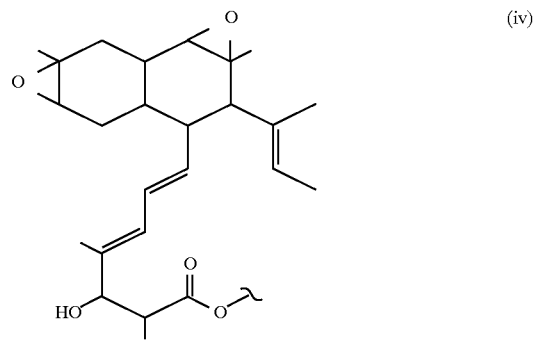

wherein $R_{xii}$ is $C_{1-6}$ alkyl, ($C_{0-6}$ alkyl) ($C_6$ aryl), or $C_{3-6}$ heteroaryl; or $R^{13}$ and $R^{14}$ taken together are =O or =$CHCH_3$ in the E or Z configuration; each of $R^{15}$ and $R^{16}$ is H, or taken together $R^{15}$ and $R^{16}$ are =O; or $R^5$ and $R^6$ together are a bivalent moiety having one of the formulae (v) and (vi):

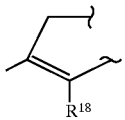

wherein $R^{17}$ is $C(O)CH_3$ or $CH(OH)CH_3$; $R^{18}$ is CHO, $CH_2OH$, $CH_2NR^fR^g$, $CH_2NR^hC(O)R^i$, $CH_2R^j$, or $CH(OC(O)CH_3)CH_3$, wherein each of $R^f$, $R^g$, and $R^h$, independently, is H, Bn, $C_{1-12}$ alkyl, $C_{6-12}$ aryl, or $C_{3-12}$ heteroaryl, $R^i$ is $C_{1-12}$ alkyl, $C_{6-12}$ aryl with 0 to 3 $C_{1-6}$ alkoxy or halogen substituents, or $C_{3-12}$ heteroaryl with 0 to 3 $C_{1-6}$ alkoxy or halogen substituents, and $R^j$ is $C_{1-12}$ alkyl, $C_{6-12}$ aryl, or $C_{3-12}$ heteroaryl; or $R^5$ and $R^6$ together are a bivalent moiety of the formula (vii):

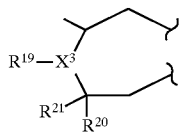

wherein $X^3$ is N or O; $R^{19}$ is H, $C_{1-12}$ alkyl, $C_{6-12}$ aryl with 0 to 2 $C_{1-6}$ alkyl substituents, $C_{3-12}$ heteroaryl with 0 to 2 $C_{1-6}$ alkyl substituents, $CH_2R_{xiii}$, $CH_2CH_2R_{xiv}$, $CH(CH_3)R_{xv}$, $CH(CH_3)CH_2R_{xvi}$, or is absent, wherein $R_{xiii}$ is $C_{1-12}$ alkyl, $C_{6-12}$ aryl with 0 to 2 $C_{1-6}$ alkoxy or halogen substituents, or $C_{3-12}$ heteroaryl with 0 to 2 $C_{1-6}$ alkoxy or halogen substituents, and each of $R_{xiv}$, $R_{xv}$ and $R_{xvi}$, independently, is $C_{1-12}$ alkyl, $C_{6-12}$ aryl or $C_{3-12}$ heteroaryl; provided that when $X^3$ is O, $R^{19}$ is absent; each of $R^{20}$ and $R^{21}$ is H, or taken together $R^{20}$ and $R^{21}$ are =O;

$R^7$ is NHBn;

$R^8$ is OH; or $R^7$ and $R^8$ taken together are —O—; and $R^9$ is one of the formulae (viii) or (ix):

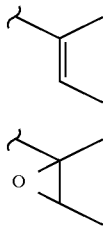

or a pharmaceutically acceptable salt thereof.

Formula (I) includes representative semisynthetic derivatives, which may be made according to standard methods of synthetic chemistry, for example, by using the natural product as a starting material.

A "substantially pure compound" or "substantially pure preparation of a compound" refers to a composition of a compound disclosed herein consisting of less than 8 percent (or less than 5 or 2.5 percent) by weight of other incidental organic molecules. Incidental organic molecules include those molecules which are naturally associated with the compound (e.g., found in a fungal isolate containing the compound) or which are reagents, reactants, side products, or decomposition products resulting from one or more synthetic transformations (e.g., an organic molecule which copurifies with the disclosed compound). A composition of a compound disclosed herein may include nonincidental organic molecules which are formulated with the compound, such as a pharmaceutically acceptable carrier, an agent to enhance absorption or bioavailability, another antifungal agent (whether disclosed herein or not), an analgesic, or an anti-inflammatory agent. The invention also encompasses derivatives of compounds within formula (I), such as pharmaceutically acceptable esters, salts, hydrates, or other solvates.

A second aspect of the invention is a method for treating mycotic infections in an organism which includes administering to an organism in need of such treatment a therapeutically effective amount of a compound having formula (I), in a pharmaceutically acceptable vehicle, thereby inhibiting a mycotic infection in the organism. An organism may be a plant or an animal, including mammals (e.g., humans, ruminants, pigs, dogs and cats) and birds (e.g., poultry).

A third aspect of the invention features a fungal isolate from which a compound of formula (I) is produced. (See Example 1). A fourth aspect of the invention provides a process for producing a compound of formula (I) from the fungal isolate. The process includes the steps of growing Aspergillus fumigatus in a fermentation broth, separating the fungal isolate from the fermentation broth or biomass, fractionating the fungal isolate, and identifying one or more fractions containing a substance having antifungal activity.

Other features and advantages of the invention will be apparent from the following detailed description and from the appending claims.

DETAILED DESCRIPTION OF THE INVENTION

A. Growth of Culture of Aspergillus fumigatus

A natural product having antifungal activity has been isolated and structurally characterized. The compound AA02769A is a natural product produced by the cultivation of a strain of Aspergillus fumigatus in the culture collection of Myco Pharmaceuticals. The organism is Aspergillus fumigatus Fresen, a common soil species. A description is found in Raper, K. B. and Fennell, D. I. (1965). *The genus Aspergillus*. Williams and Wilkins, pages 242–244. The fungus has been deposited under the Budapest Treaty in the culture collection of the American Type Culture Collection at 12301 Parklawn Drive, Rockville, Md. 20852, and has been assigned the accession number ATCC 74346.

Applicants' assignee, Myco Pharmaceuticals, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

B. Separation, Fractionation and Isolation

General information for growing *A. fumigatus* is provided in Example 1. The fungal isolate is separated from the fermentation broth or biomass by any of the well-known methods such as continuous extraction, filtration, or a combination thereof.

Fractionation of the fungal isolate can be accomplished by any of several standard biochemical methods, including HPLC, gel filtration, affinity chromatography, and ion exchange chromatography.

The isolation and structural characterization of AA02769A is detailed below in Example 1. Exemplary methods of synthesizing derivatives of AA0276A are in the next section (Section C).

Certain terms used herein are defined below, and by their usage in this disclosure. For example, Ac is acetyl, Bz is benzoyl, and Bn is benzyl.

The term alkyl includes straight chain, branched, and cyclic alkyl groups. For example, $C_{1-6}$ alkyl includes methyl, ethyl, propyl, isopropyl, cyclopropyl, butyl, isobutyl, sec-butyl, t-butyl, cyclobutyl, neo-pentyl, hexyl, and isohexyl.

An aryl group is a $C_{6-40}$ aromatic ring, wherein the ring is made of carbon atoms (e.g., $C_{6-20}$, $C_{6-12}$, or $C_{6-10}$ aryl groups). Examples include phenyl, halo-substituted phenyl, benzyl (Bn), naphthyl, binaphthyl, azulyl, indyl, pentalyl, phenanthrenyl, and biphenylyl. For example, the term $C_8$ aryl includes alkylaryls, alkenylaryls, alkynylaryls, arylalkenyls, arylalkynyls, and arylalkyls such as 4-methylbenzyl, 3-ethylphenyl, 4-vinylphenyl (4-ethenylphenyl), and 2,3-dimethylphenyl. The analogous relationship of heteroaryls applies below.

A heterocyclic radical contains at least one ring structure which contains carbon atoms and at least one heteroatom such as N, O, or S. A heteroaryl is an aromatic heterocyclic radical. Examples of heterocyclic radicals and heteroaryl groups include: thiazolyl, 2-thienyl, 3-thienyl, 3-furyl, furazanyl, 2H-pyran-3-yl, 1-isobenzofuranyl, 2H-chromen-3-yl, 2H-pyrrolyl, N-pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, phthalazinyl, cinnolinyl, and pteridinyl. For example, a $C_{3-12}$ heteroaryl group may be a $C_{3-6}$, or a $C_{4-9}$ group. A heterocyclic or heteroaryl radical may be attached to another moiety via a carbon atom or a heteroatom of the radical.

The structures disclosed herein contain chiral centers. Unless otherwise indicated, drawn structures include both (R) and (S) stereoisomers at each chiral center. During isolation and subsequent synthetic transformations, if any, it may be desirable to resolve the racemates via chiral reagents, chiral chromatography, or other techniques in asymmetric synthesis and separation. In certain embodiments, an (R) center is preferred; in other embodiments, an (S) center is preferred. The E (entgegen) and Z (zusammen) configurations relative to a carbon-carbon double bond are known to those in the art.

The invention also encompasses compounds that have the disclosed structures except that one or more conventional protecting groups are used, such as hydroxyl protecting groups, carboxylate protecting groups, and carbonyl protecting groups. Methods of adding and removing such protecting groups are well known in the art (see, for example, Protective *Groups in Organic Synthesis,* by T. W. Greene and P. G. M. Wuts, 2nd ed., 1991, Chapters 2, 4, and 5).

C. Synthesis of AA02769A Derivatives

Using the purified AA02769A as a starting material, representative simple derivatizations of AA02769A are described in Example 3. This section outlines chemical methods to produce more complex derivatives of AA02769. Scheme I below shows the structures of compounds AA02769A, C, D, and E.

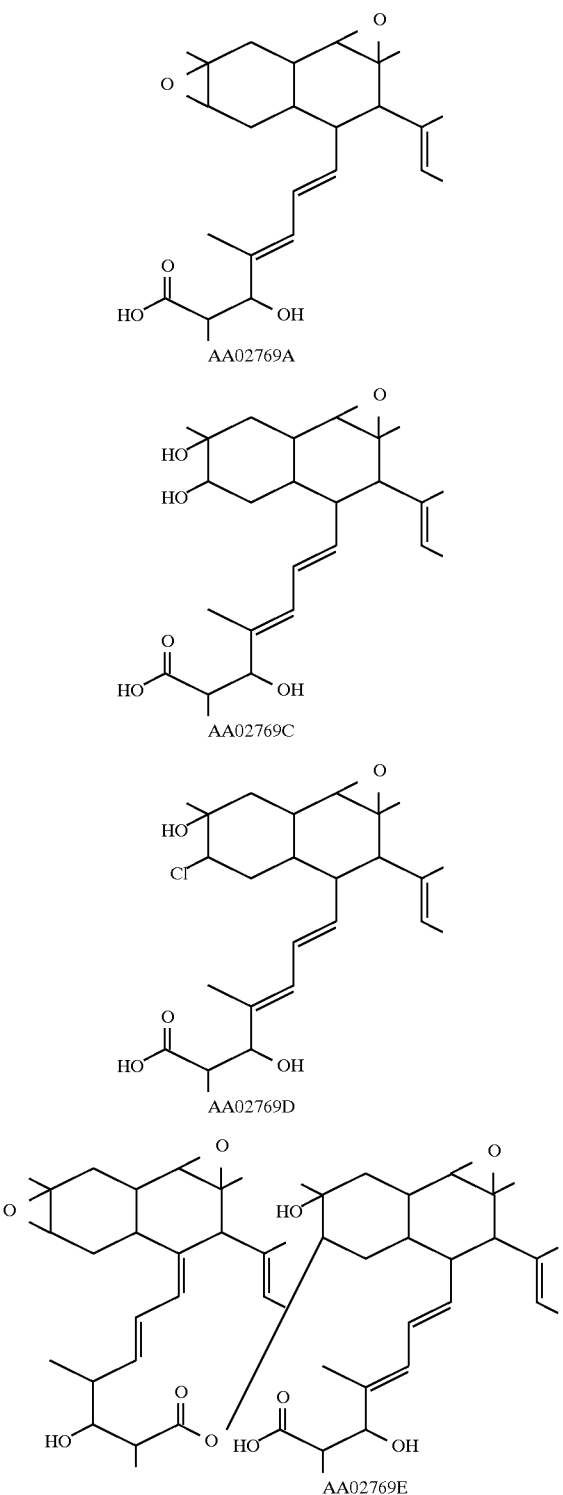

Scheme I

The reaction of AA02769A with an excess of diazomethane, which is generated from Diazald (N-methyl-N-nitroso-p-toluenesulfonamide), in an inert solvent such as methanol or diethyl ether at ambient temperature yields the corresponding methylated compound (1).

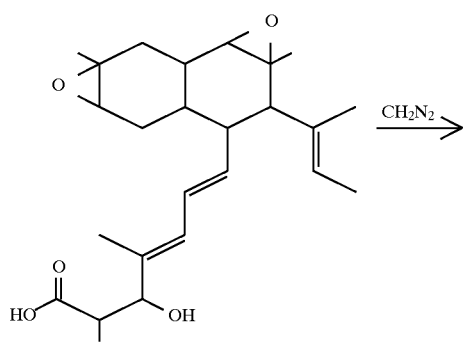

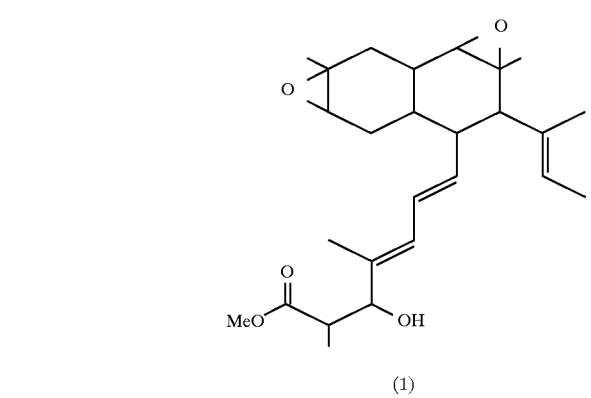

(1)

The reaction of AA02769A with two equivalents of pyridine and acetic anhydride at ambient or elevated temperature followed by removal of the solvents as volatiles in vacuo yields the corresponding bis-acetylated compound (2); aqueous partition of (2) yields the corresponding monoacetylated compound (3).

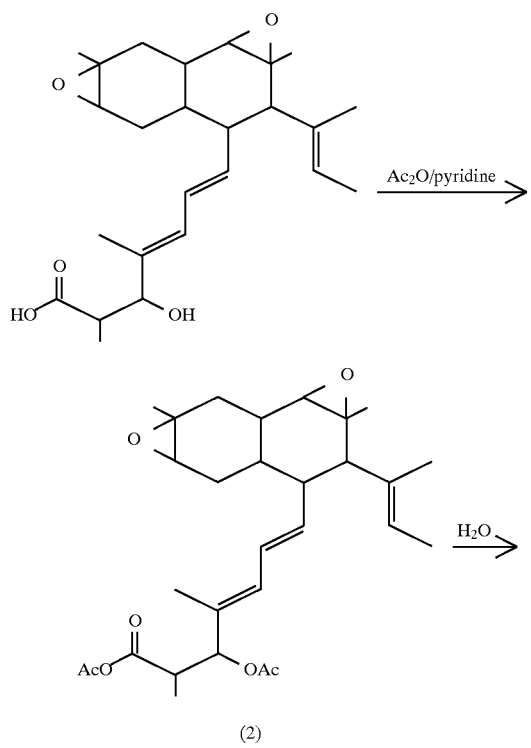

(2)

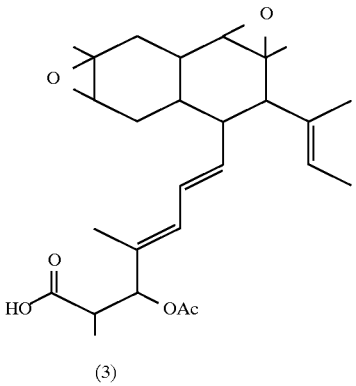

(3)

The reaction of AA02769A with one equivalent of dicyclohexyl carbodiimide (DCC) in an inert solvent such as THF, $CH_2Cl2$, or dioxane, followed by the addition of 1 equivalent of ammonia or an alkylamine, yields the corresponding amide (4).

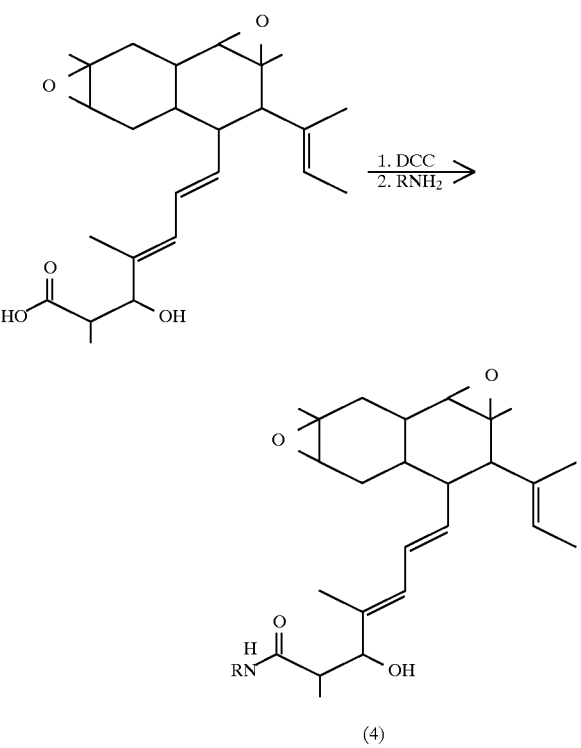

(4)

The reaction of AA02769A with one equivalent of acetic anhydride and pyridine followed by one equivalent of phosphorus oxychloride ($POCl_3$) in a solvent such as $CHCl_3$, $CCl_4$, or $CH_2Cl_2$ at ambient or elevated temperatures, followed by removal of the solvent in vacuo, yields the corresponding acid chloride (5). This compound can be used to prepare other derivatives, including the amide (4), by reaction with ammonia.

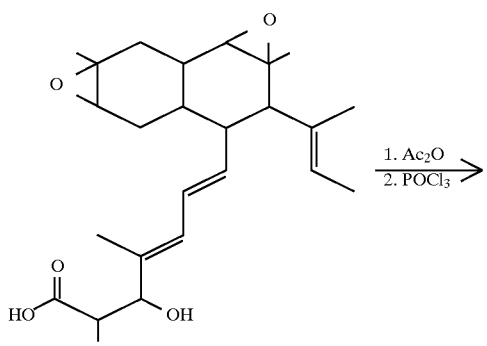

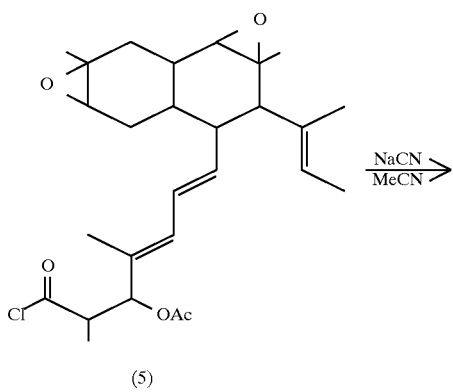

The reaction of acid chloride (5) in an inert solvent such as acetone, acetonitrile, dichloromethane, or dioxane, with one or more equivalents of a cyanide salt such as sodium cyanide, with or without a catalyst such as 18-crown-6, yields the corresponding acyl cyanide (6).

The reaction of AA02769A with two or more equivalents of phosphorus pentachloride in an inert solvent such as carbon tetrachloride at ambient or elevated temperature, with or without added base, followed by aqueous workup yields the corresponding chloride (7).

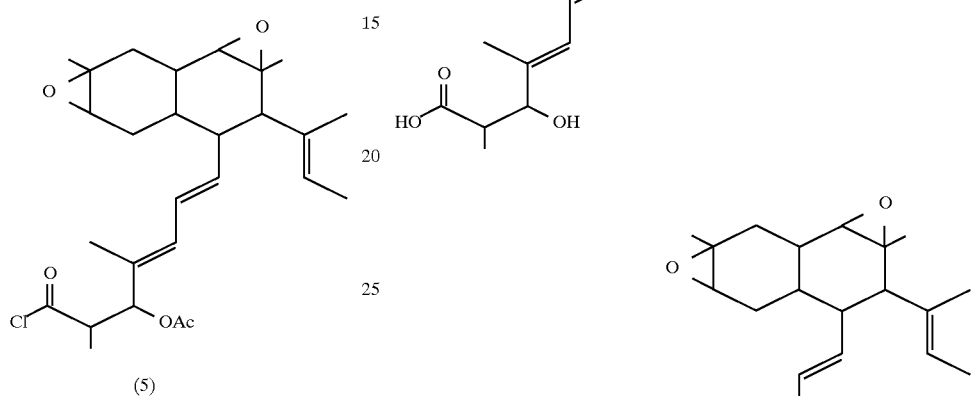

Sequential reaction of compound AA02769A with diazomethane, followed by methyl (triphenoxy) phosphonium iodide in dimethylformamide, followed by aqueous workup, yields iodocompound (8).

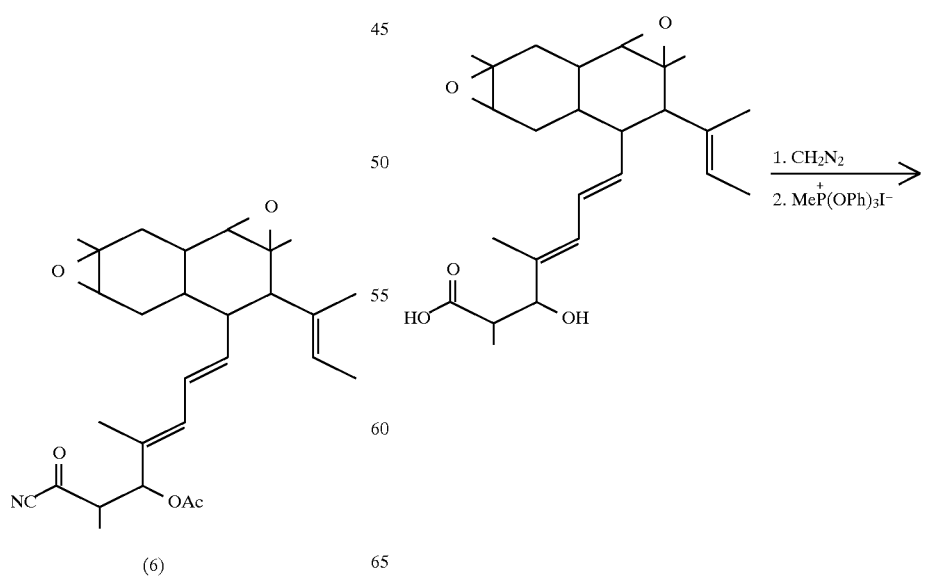

-continued

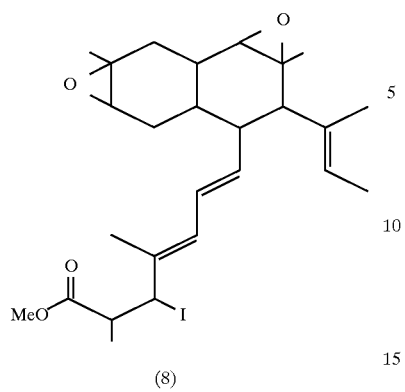

(8)

The reaction of iodocompound (8) with an excess of a salt of hydrazoic acid, such as sodium azide, in an inert, dipolar, aprotic solvent, such as DMF, N-methylpyrrolidinone, DMPU, or DMSO, yields azide (9).

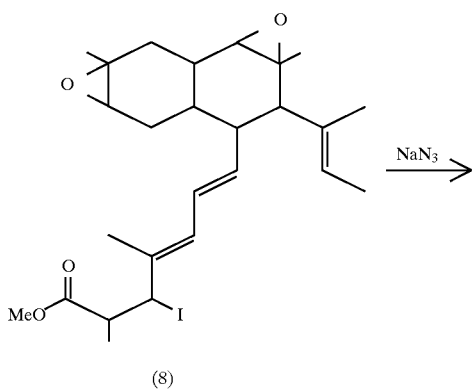

(9)

The reaction of iodocompound (8) with an excess of a metal cyanide salt such as potassium cyanide in an inert solvent such as acetonitrile, with or without a catalyst such as 18-crown-6, followed by an aqueous workup, yields nitrile (10).

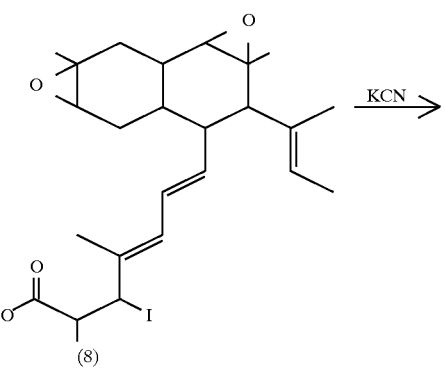

(8)

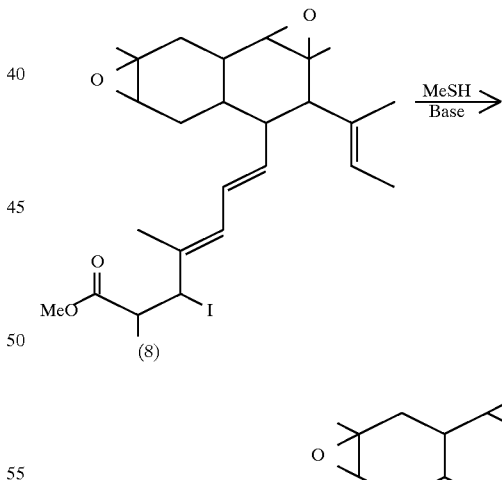

(10)

The reaction of iodocompound (8) with one or more equivalents of an alkanethiol, such as methanethiol, with or without added base such as trialkylamines, DABCO, DBU, DBN, potassium carbonate, or potassium t-butoxide, in an inert solvent such as acetonitrile or DMF, yields the thioether (11) after aqueous workup.

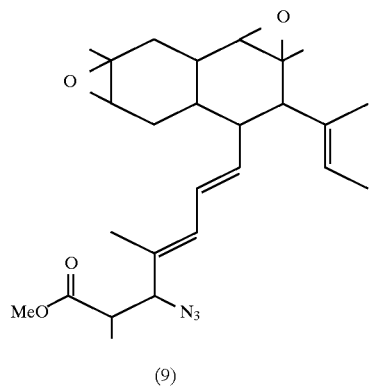

(8)

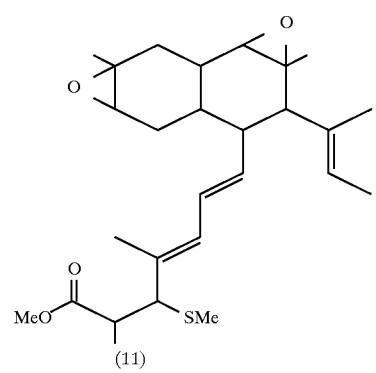

(11)

Combinatorial chemistry can be applied to the creation of thioethers related to (11). These may be generated as mixtures of related compounds by substituting a mixture of alkylthiols for the methanethiol, or by reacting (8) with individual thiols in a 96-well plate. For example, the reaction of (8) (1 mmol) with a mixture of: methanethiol (0.1 mmol), ethanethiol (0.1 mmol), butanethiol (0.1 mmol), thioacetic acid (0.1 mmol), thiophenol (0.1 mmol), 1-thionaphthalene (0.1 mmol), 1,3-propane-dithiol (0.1 mmol), 3,3-dimethyl propanethiol (0.1 mmol), 3-thiopropionic acid (0.1 mmol), and 2-thiopropionic acid (0.1 mmol) in the presence of potassium t-butoxide (1.0 mmol) yields a mixture of (11) and 10 other thioether analogs, since 1,3-propane-dithiol can add once or twice to (8). The reaction of AA02769A with dilute aqueous acid yields the corresponding diol (12).

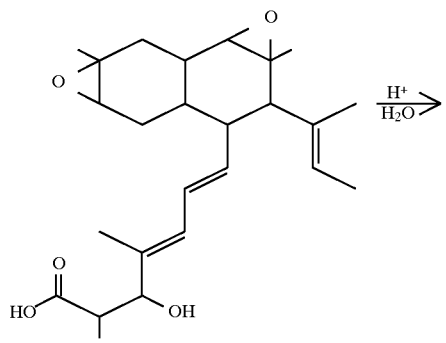

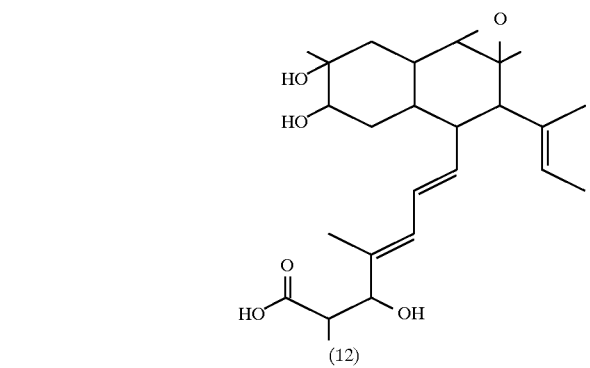

The reaction of diol (12) with diazomethane, followed by an excess of sodium periodate in an inert solvent such as diethyl ether yields the corresponding compound (13).

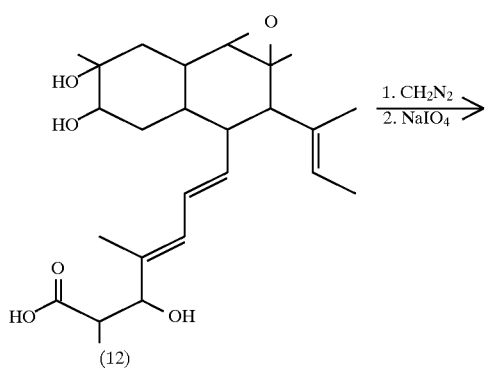

-continued

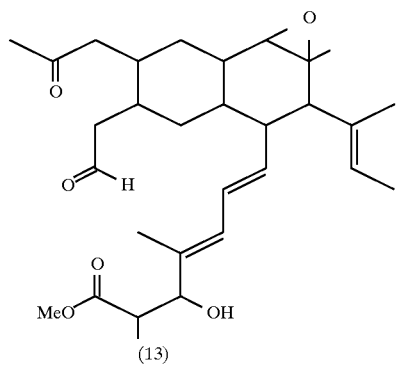

The reaction of compound (13) with one equivalent of hydroxylamine-o-sulfate, followed by aqueous workup, yields the corresponding cyanide (14).

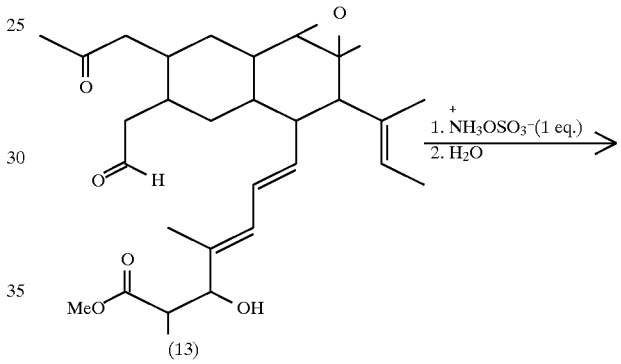

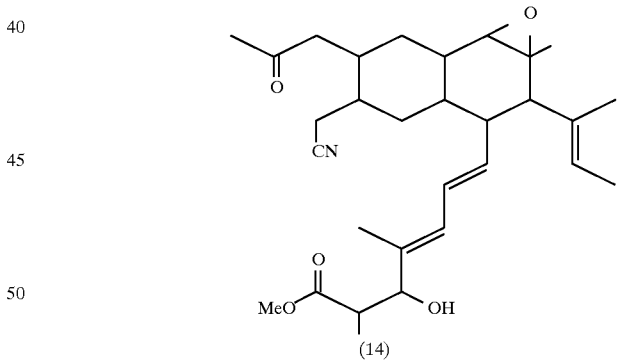

The reaction of compound (13) with a primary amine, followed by reduction with sodium cyanoborohydride in a solvent such as dilute acetic acid, yields the cyclic amine (15).

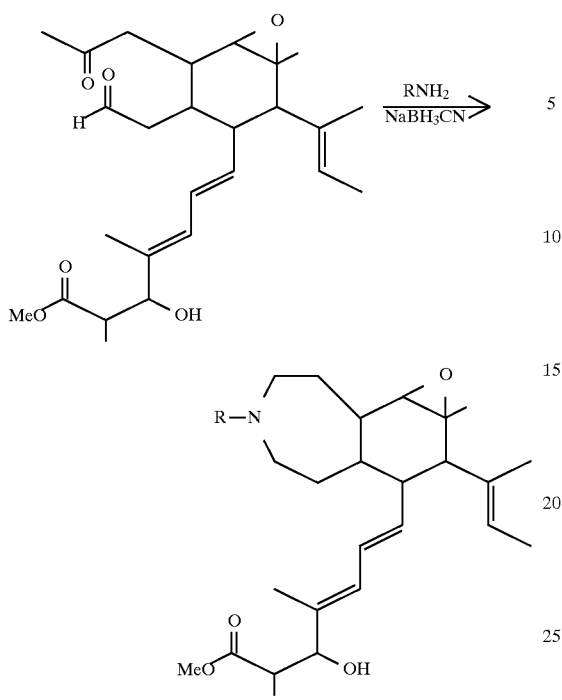

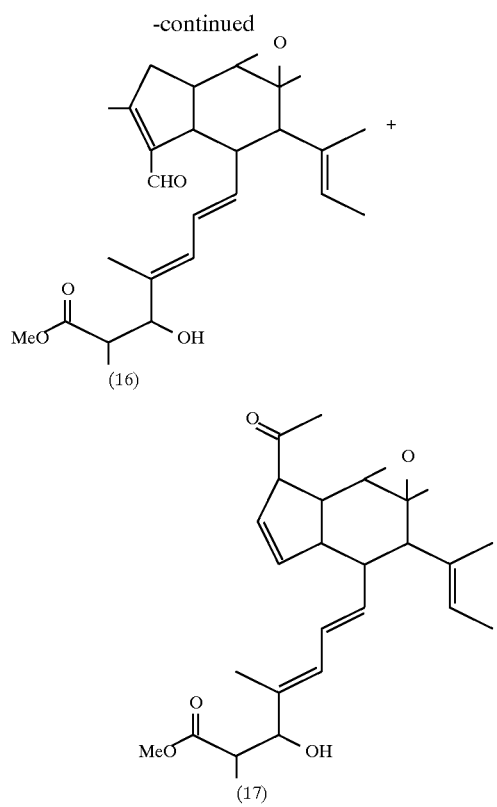

The reaction of (13) (1 mmol) with a mix of: methylamine (0.1 mmol), propylamine (0.1 mmol), butylamine (0.1 mmol), benzylamine (0.1 mmol), 4-chlorobenzylamine (0.1 mmol), 3-methoxybenzylamine (0.1 mmol), amphetamine (0.1 mmol), α-phenethylamine (0.1 mmol), 2-phenethylamine (0.1 mmol), 2-aminomethylfuran (0.1 mmol), according to the general conditions used to prepare (15), leads to 10 related compounds.

The reaction of compound (13) with a base such as sodium methoxide in methanol yields the α,β-unsaturated compounds (16) and (17).

The reaction of compound (13) with tert-butyldimethylsilyl chloride in an inert solvent such as dimethylformamide, followed by reduction with sodium borohydride, followed by the addition of p-toluenesulfonyl chloride, followed by the addition of a base such as pyridine, followed by the addition of tetra-n-butylammonium fluoride in an inert solvent such as tetrahydrofuran, yields the corresponding cyclic ether (18).

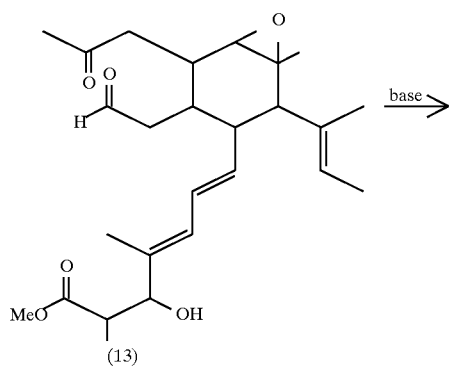

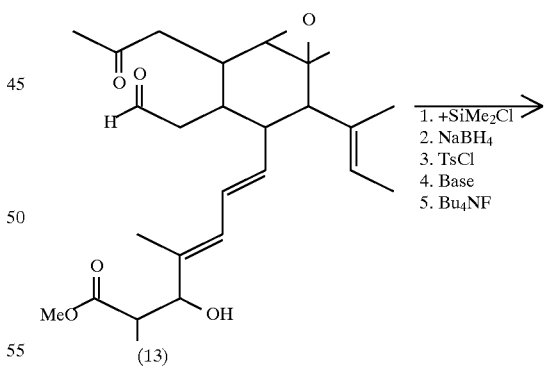

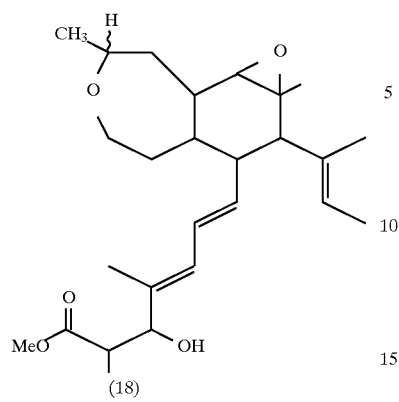

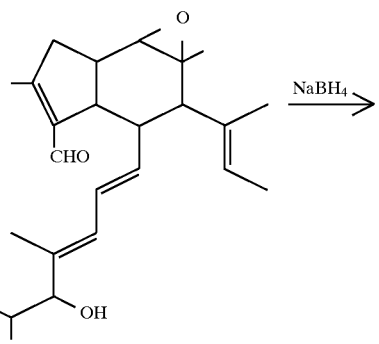

The reaction of cyanide (14) with an excess of an amine, followed by reduction with sodium cyanoborohydride in dilute aqueous acetic acid, yields the corresponding amine (19), which is conveniently isolated as the hydrochloride salt.

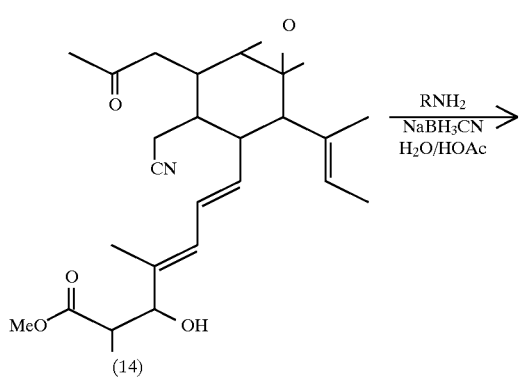

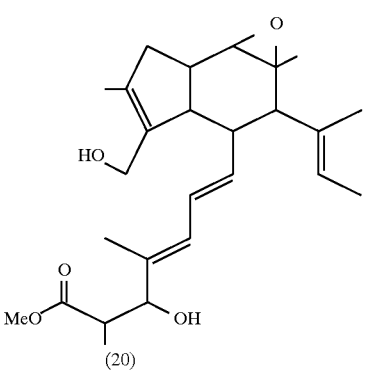

The reaction of α,β-unsaturated aldehyde (16) with an amine, followed by reduction with sodium cyanoborohydride in dilute aqueous acid, yields the corresponding amine (21), which is conveniently isolated as the hydrochloride salt.

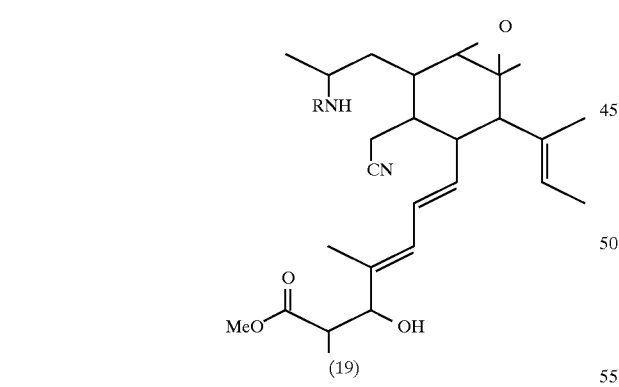

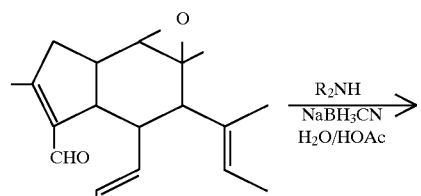

The reduction of α,β-unsaturated aldehyde (16) with sodium borohydride in an inert solvent such as THF yields the corresponding alcohol (20).

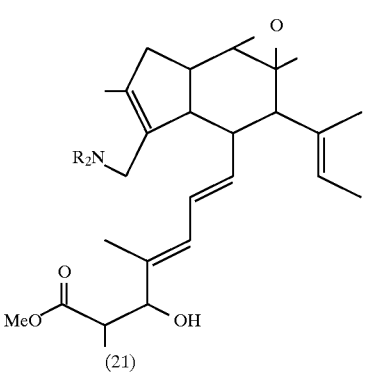

The reaction of aldehyde (16) (1.0 mmol) with a mixture of amines: N,N-dimethylamine (0.1 mmol), N,N-diethylamine (0.1 mmol), N-ethyl-N-methylamine (0.1 mmol), N-methyl benzylamine (0.1 mmol), N-methylaniline (0.1 mmol), N,N-dibenzylamine (0.1 mmol), N-propyl benzylamine (0.1 mmol), N-methylcyclohexylamine (0.1 mmol), N-butylaniline (0.1 mmol), α-methyl-1-naphthylamine (0.1 mmol), according to the general conditions used to prepare compound (21), yields 10 related compounds.

The reduction of α,β-unsaturated ketone (17) with sodium borohydride in an inert solvent such as THF yields the corresponding alcohol (22).

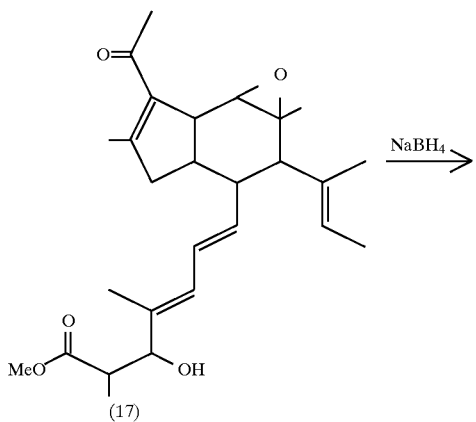

(17)

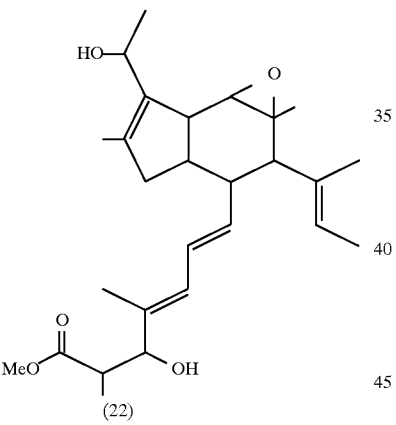

(22)

The reaction of amine (21) with an anhydride (1 equivalent) and a base such as a trialkylamine in an inert solvent such as methylene chloride yields the corresponding amide (23).

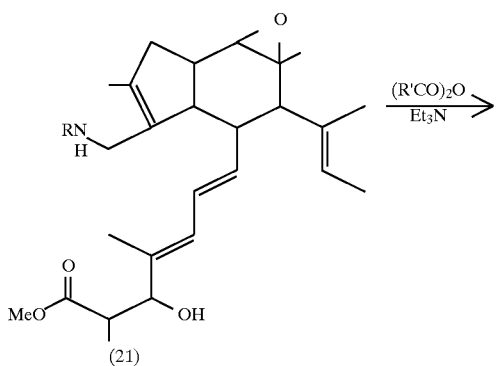

(21)

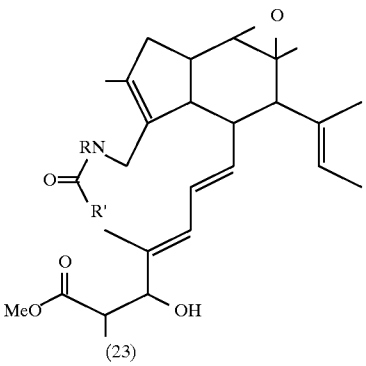

(23)

The reaction of (21) with a mixture of anhydrides and a base such as triethylamine yields a family of amides (23). For example, the reaction of (21) (1.0 mmol) with the following mixture of anhydrides: acetic anhydride (0.1 mmol), propionic anhydride (0.1 mmol), benzoic anhydride (0.1 mmol), 4-chlorobenzoic anhydride (0.1 mmol), 3-methoxybenzoic anhydride (0.1 mmol), phenylacetic anhydride (0.1 mmol), 1-naphthalene acetic anhydride (0.1 mmol), trifluoroacetic anhydride (0.1 mmol), chloroacetic anhydride (0.1 mmol), 2-acetoxypropionic anhydride (0.1 mmol), yields 10 analogs.

The reaction of AA02769A with an excess of diazomethane, followed by the addition of dilute aqueous acid which brings about regiospecific epoxide opening, followed by the addition of tert-butyldiphenylsilyl chloride in dimethylformamide, yields the corresponding diol (24).

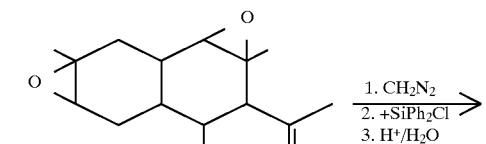

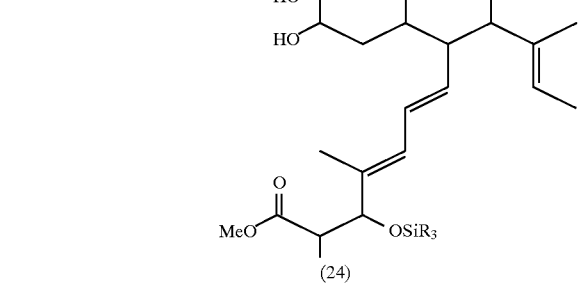

(24)

The oxidation of diol (24) with N-methylmorpholine-N-oxide catalyzed by tetrapropylammonium perruthenate, in an inert solvent such as THF, followed by the addition of methanesulfonyl chloride and a base such as a trialkylamine in diethyl ether, followed by the addition of a base such as a trialkylamine, yields the a,f-unsaturated ketone (25).

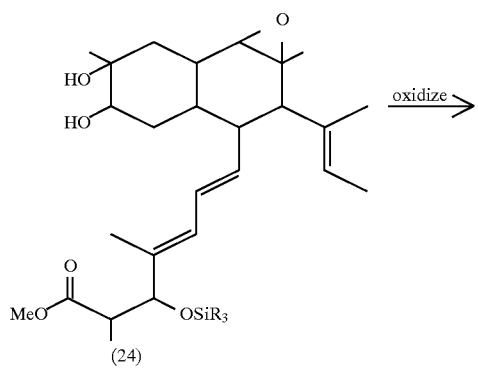

(24)

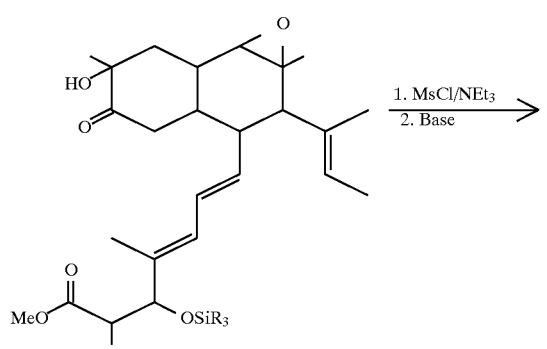

(25)

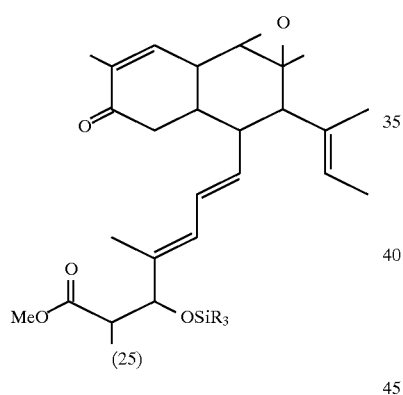

(25)

The reaction of α,β unsaturated ketone (25) with an amine in an inert solvent such as methylene chloride yields the corresponding amine (26).

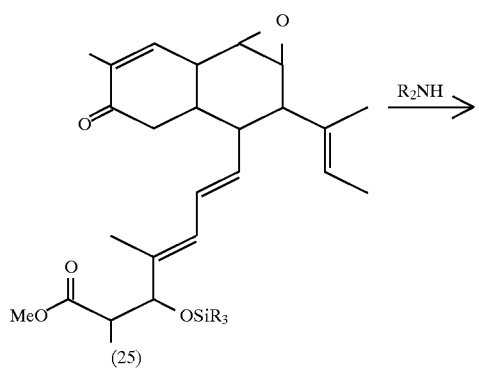

(25)

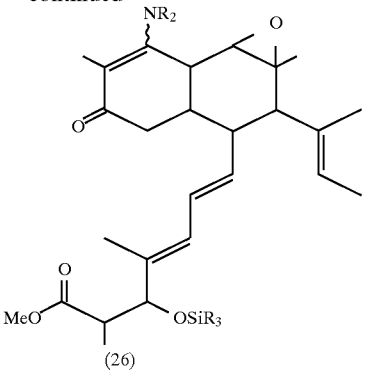

(26)

The reaction of (25) with a mixture of amines in an inert solvent yields the corresponding amine compounds. For example, the reaction of (25) (1 mmol) with the following mixture of amines: methylamine (0.083 mmol), n-butylamine (0.083 mmol), t-butylamine (0.083 mmol), benzylamine (0.083 mmol), N-methylbenzylamine (0.083 mmol), α-methyl-benzylamine (0.083 mmol), dimethylamine (Q.083 mmol), N-methyl-2-phenethylamine (0.083 mmol), 4-bromo-2-phen- ethylamine (0.083 mmol), cyclopropylamine (0.083 mmol), N-methylaniline (0.083 mmol), N,N-ethylpropylamine (0.083 mmol), yields 12 new analogs.

The reaction of α,β-unsaturated ketone (25) with a thiol and a base such as a trialkylamine in an inert solvent such as methylene chloride yields the corresponding sulfide (27).

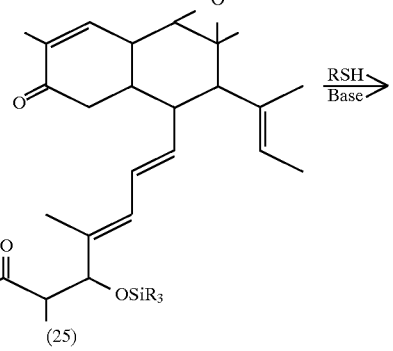

(25)

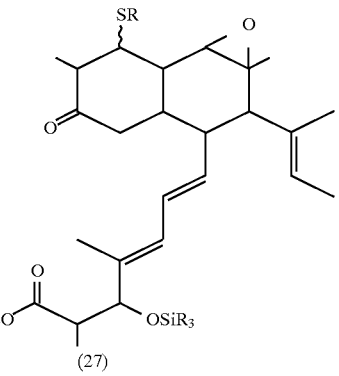

(27)

The reaction of (25) (5.0 mmol) with the following 5 thiols: methanethiol (1.0 mmol), thiophenol (1.0 mmol), propanethiol (1.0 mmol), butanethiol (1.0 mmol), benzylthiol (1.0 mmol), yields the corresponding 5 thioether analogs.

The reaction of α,β-unsaturated ketone (25) with hydrogen peroxide and a base such as potassium t-butoxide, followed by the addition of toluenesulfonylhydrazine, followed by the addition of sodium borohydride, followed by the addition of p-toluenesulfonyl chloride, followed by the addition of sodium sulfide, followed by a base such as pyridine, yields the cyclic sulfide (28).

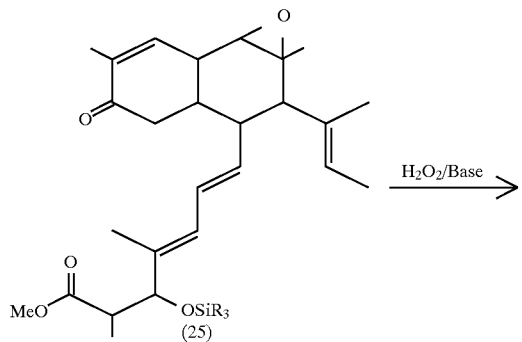

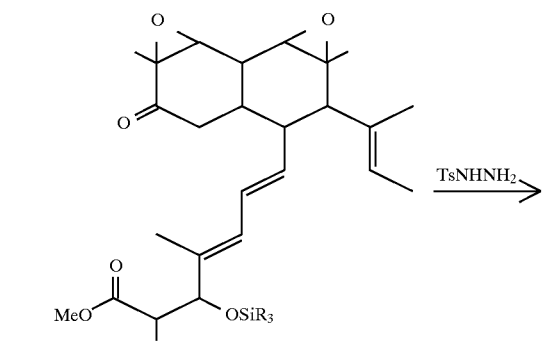

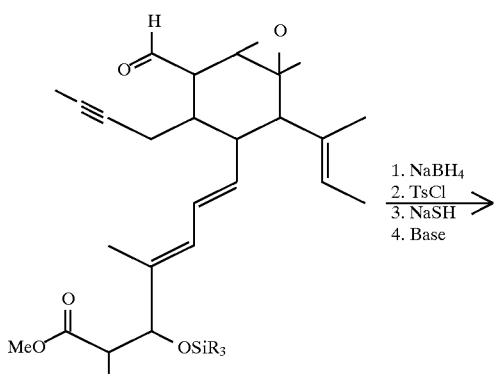

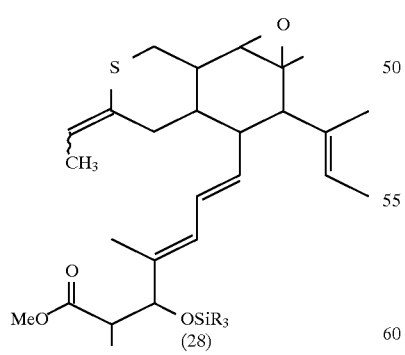

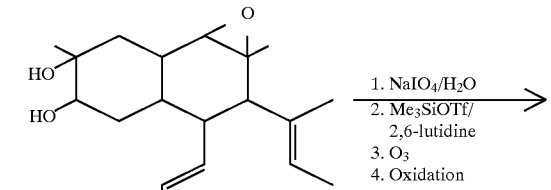

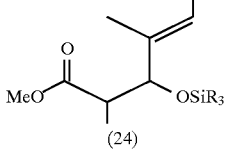

The reaction of compound (29) with acetic anhydride and 4-dimethylaminopyridine in pyridine yields the corresponding compound (30).

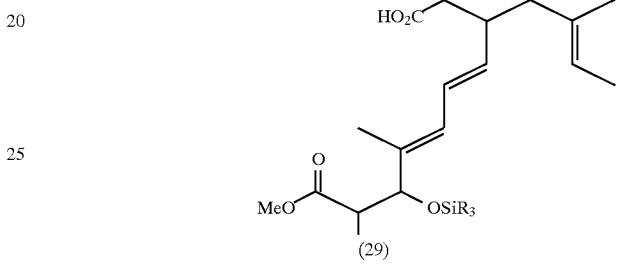

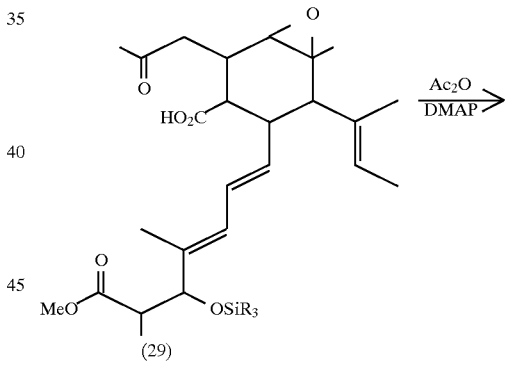

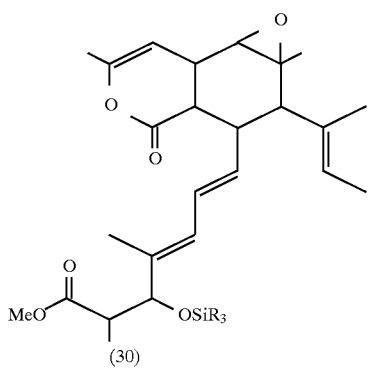

The reaction of diol (24) with sodium periodate in water, followed by reaction with trimethylsilyl triflate/lutidine and ozonolysis, followed by oxidation yields the corresponding compound (29).

The reaction of diol (24) with sodium periodate and potassium permanganate, then dicyclohexyl carbodiimide in methylene chloride, followed by the addition of hydroxylamine, followed by the addition of p-toluenesulfonyl chloride and a base such as a trialkylamine, followed by hydrolysis with dilute aqueous acid and by the addition of sodium borohydride in an inert solvent such as diethyl ether, yields the cyclic amine (31).

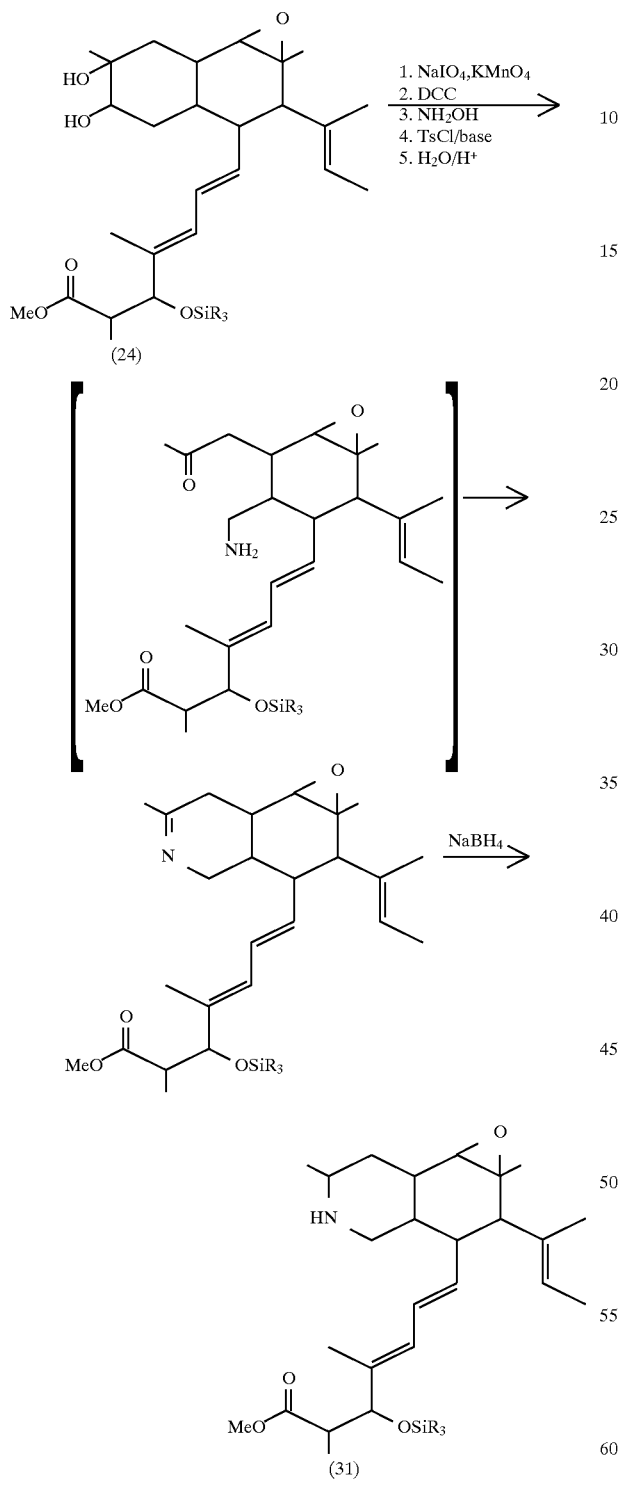

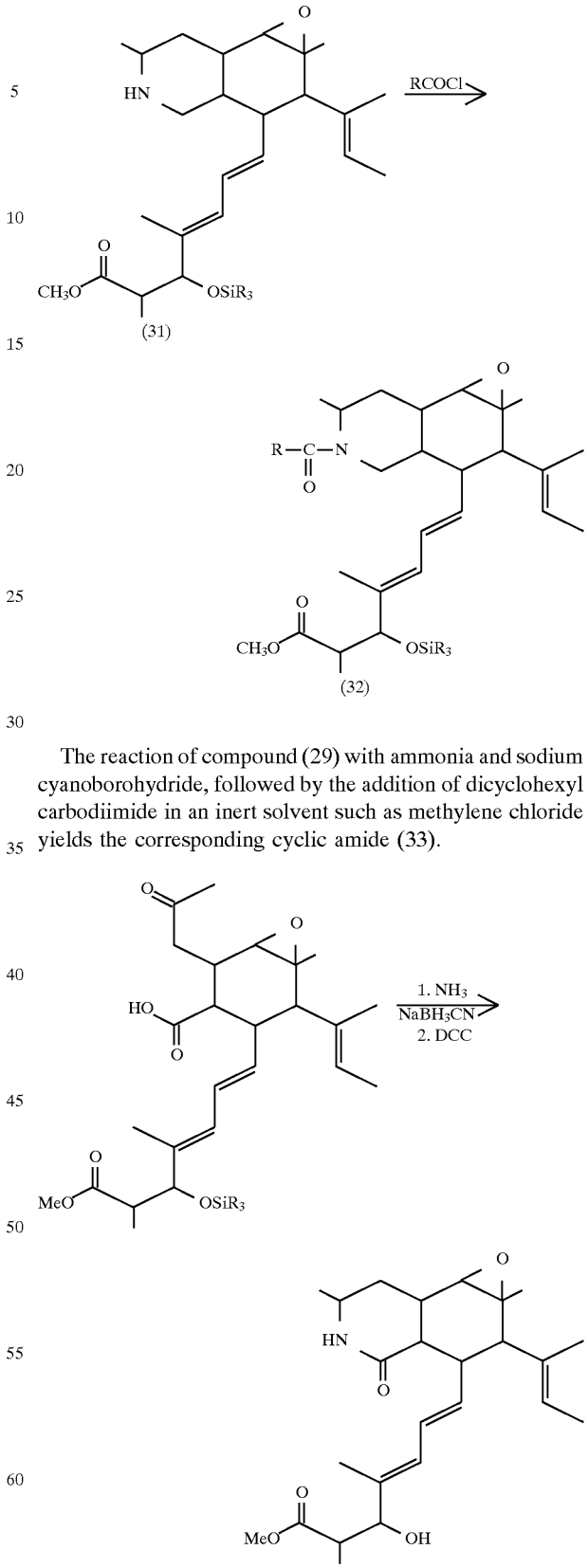

The reaction of compound (29) with ammonia and sodium cyanoborohydride, followed by the addition of dicyclohexyl carbodiimide in an inert solvent such as methylene chloride yields the corresponding cyclic amide (33).

The reaction of amine (31) with an acid chloride and a base such as pyridine in an inert solvent such as methylene chloride yields the corresponding amide (32).

The reaction of AA02769A with lithium aluminum hydride in ether yields the diol (34) and the triol (35).

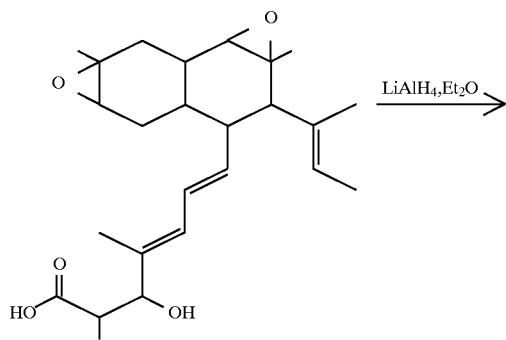

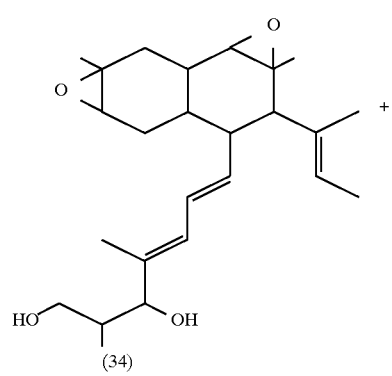

(34)

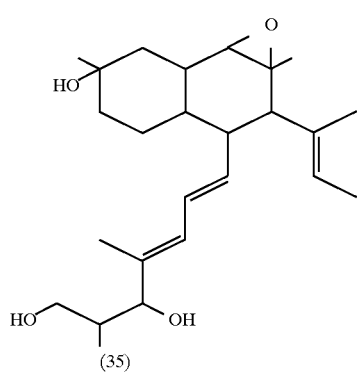

(35)

The reaction of AA02769A with benzylamine, followed by dicyclohexyl carbodiimide and 4-dimethylaminopyridine in methylene chloride, yields compound (36).

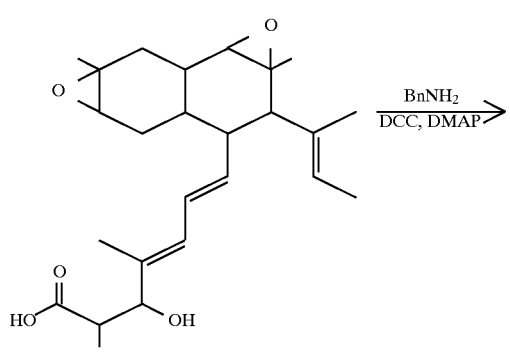

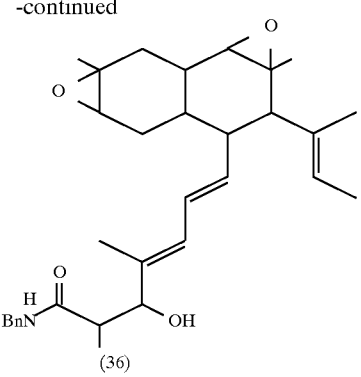

(36)

The reaction of AA02769A with methylamine, followed by dicyclohexyl carbodiimide and 4-dimethylaminopyridine in methylene chloride, yields compound (37).

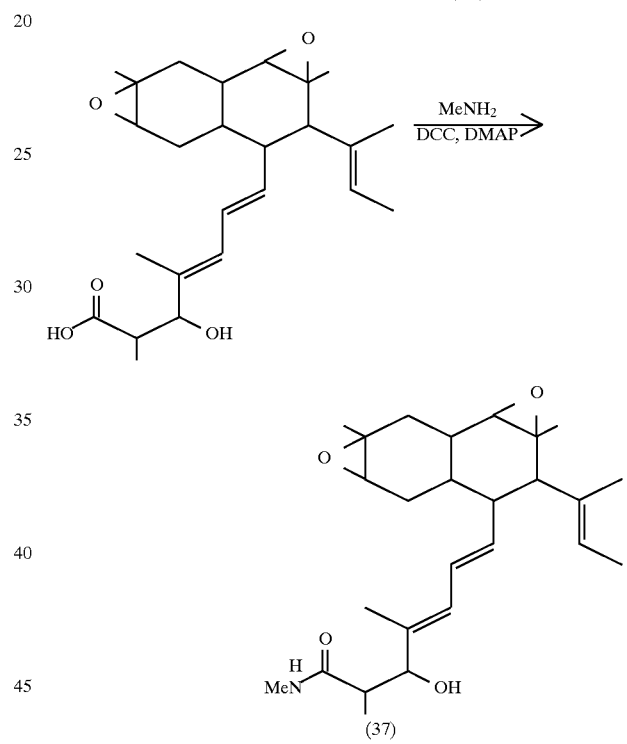

(37)

The reaction of AA02769A with diphenylphosphoryl azide, triethylamine, and glycine methyl ester hydrochloride yields compound (38).

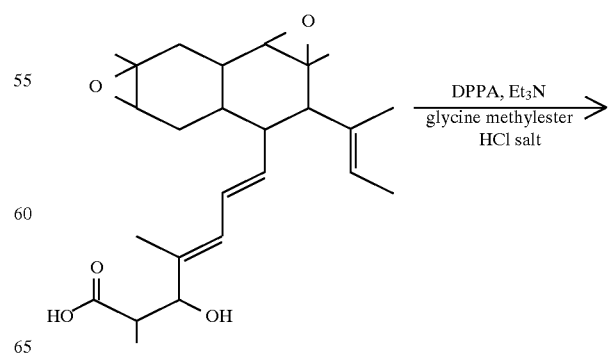

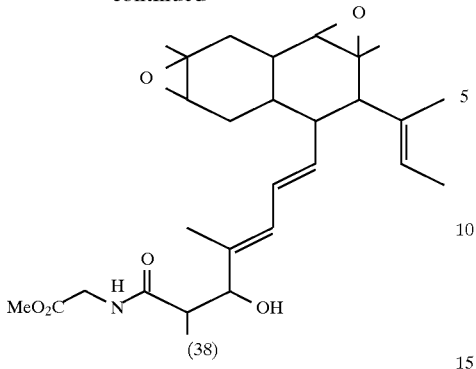

(38)

The reaction of AA02769A with diphenylphosphoryl azide and triethylamine in t-butanol at an elevated temperature yields compound (39).

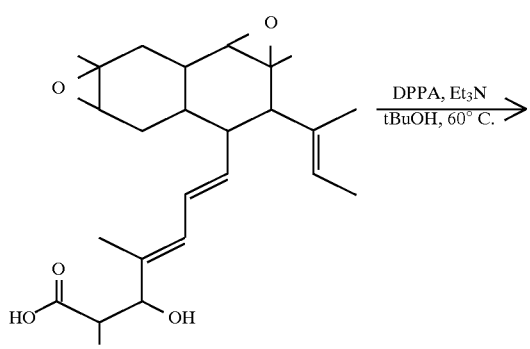

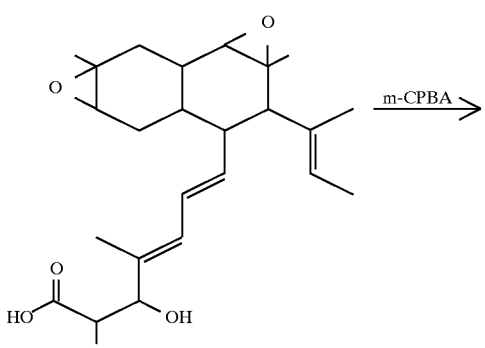

The reaction of AA02769A with m-chloroperoxybenzoic acid in an inert solvent such as THF yields the tris-epoxide (40).

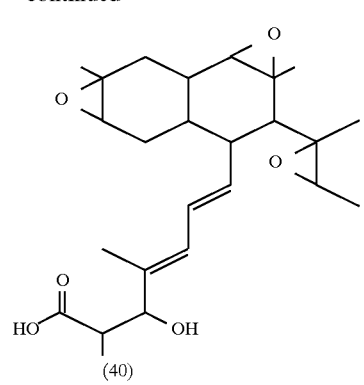

(40)

The reaction of AA02769A with benzylamine in an inert solvent such as methylene chloride yields compound (41).

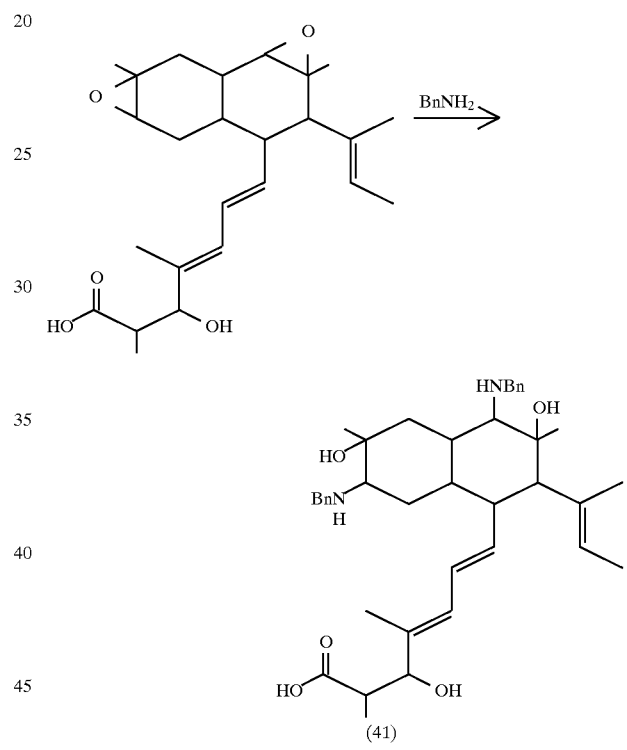

(41)

In addition to the compounds described herein, the invention also encompasses esters of disclosed compounds. Since many of the disclosed compounds contain at least one hydroxyl group and at least one carboxylic acid group, the invention encompasses condensation products (esters) equivalent to the reaction of (a) a disclosed compound having a carboxylic acid group and a $C_{1-2}$ alcohol (e.g., $C_{1-6}$ alkanol, including methanol, ethanol, and butanol) or a $C_{10}$-, $C_{15}$-, or $C_{20}$ terpenoid; (b) a first disclosed compound having a carboxylic acid and a second disclosed compound having a hydroxyl group, wherein the first and second disclosed compounds may be the same or different; (c) a disclosed compound having a hydroxyl group and a $C_{1-12}$ carboxylic acid (e.g., $C_{1-6}$ carboxylic acid).

The invention also encompasses amides of the disclosed compounds. These amides may be formed by reacting a disclosed compound with any naturally-occurring amino acid, an oligopeptide having up to 10 (e.g., 4, 3, or 2) residues, a peptidomimetic having a molecular weight less than 300, or any $C_{1-20}$ organic moiety having an amino group that is not already described above. The term "naturally occurring amino acid" is meant to include the 20 common a-amino acids (Gly, Ala, Val, Leu, Ile, Ser, Thr, Asp, Asn, Lys, Glu, Gln, Arg, His, Phe, Cys, Trp, Tyr, Met and Pro), and other amino acids that are natural products, such as norleucine, ethylglycine, ornithine, methylbutenyl-methylthreonine, and phenylglycine. Examples of amino acid side chains include H (glycine), methyl (alanine), —$CH_2$—(C=O)—$NH_2$ (asparagine), —$CH_2$—SH (cysteine), and —CH(OH)$CH_3$ (threonine).

D. Assays

Biologically active fractions are identified by means known to those in the art such as an enzyme inhibition assay, a whole-cell fungal growth inhibition assay, a protein binding assay, and a DNA binding assay (see Example 2). For example, an agar dilution assay identifies a substance which inhibits fungal growth. Microtiter plates are prepared with serial dilutions of the test sample; adding to the preparation a given amount of growth substrate; and providing a preparation of spores or filamentous fungi to be cultured on the prepared substrate. Spores of filamentous fungi may be selected, for example, from Aspergillus, Blastomyces, and Cryptococcus, and species listed in the Background section. Inhibition of growth is determined, for example, by observed changes in optical densities of the cultures.

An organism may suffer from more than one type of mycotic or fungal infection. Inhibiting mycotic or fungal growth therefore includes inhibiting at least one type of mycotic infection. Such inhibition can be measured by comparative methods known to those in the art, such as but not limited to the assays described in Example 2. Inhibition is demonstrated, for example, by comparing (in the presence and absence of a compound of the invention) the rate of growth or the absolute growth of fungal sporulation or nuclei; or by measuring a metabolite or signal molecule correlated with fungal growth or sporulation. Inhibition includes a reduction of one of the above measurements by at least 20% (e.g., at least 25%, 30%, 40%, 50%, 75%, 80%, or 90%). Organisms include an animal such as a mammal, and particularly a human; a plant, e.g., a food crop for human or animal nutrition; or an animal or plant cell or tissue culture.

B. Use

It is an object of the invention to provide therapeutically effective compositions of one or more disclosed compounds for use in treatment of mycotic infections in mammals, including humans, plants, and non-mammal animals. One aspect of the invention is a method for treating fungal infection in a mammal, animal or plant subject. Such a treatment includes administering a pharmaceutically effective amount of a composition containing a compound disclosed herein to a subject in need of such treatment, thereby inhibiting fungal growth in the subject. A composition contains from about 0.1 to 90% by weight (such as about 1 to about 20% or about 1 to 10%), of an active compound of the invention.

Solid formulations of the compositions for oral administration may contain suitable carriers or diluents such as corn starch, gelatin, lactose, acacia, sucrose, microcrystalline cellulose, kaolin, mannitol, dicalcium phosphate, calcium carbonate, sodium chloride, and alginic acid. Disintegrators that can be used include micro-crystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method whereby a pharmaceutical formulation containing the antifungal and a physiologically acceptable diluent is infused. Physiologically acceptable diluents may include, for example, 5% dextrose, 0.9% saline, Ringer's solution or other suitable diluents. Intramuscular preparations, a sterile formulation of a suitable soluble salt form of the compounds can be dissolved and administered in a pharmaceutical diluent such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g. ethyl oleate).

A topical semi-solid ointment formulation will contain a concentration of the active ingredient from about 1 to 20%, preferably 5 to 10% in a carrier such as a pharmaceutical cream base. The formulation for topical use includes drops, tinctures, lotions, creams, solutions, and ointments containing the active ingredient and various supports and vehicles.

The percentage of active ingredient in each pharmaceutical formulation varies according to the formulation itself and the therapeutic effect desired in the specific pathologies and correlated therapeutic regimens.

The effective amount of the active compound used to practice the present invention for treatment of conditions caused by or contributed to by fungal infection varies depending upon the manner of administration, the age and the body weight of the subject and the condition of the subject to be treated, and ultimately will be decided by the attending physician, veterinarian, or botanist. Such amount of the active compound as determined by the attending physician, veterinarian, or botanist is referred to herein as "effective amount."

Without further elaboration, it is believed that based on the description herein, the present invention can be utilized to its fullest extent. The following specific examples are, therefore illustrative, and not limitative of the remainder of the disclosure. All publications cited herein are hereby incorporated by reference.

EXAMPLE 1

Small aliquots (2 mL) of seed culture are stored in liquid nitrogen at less than −130° C. in 10% glycerol as cryoprotectant. Typically, 1 ampule was thawed and the contents passed into 50 mL Myco media 5 (MM5). MM5 media is composed of 50% (v/v) V-8 juice (Campbell Soup Co., Camden, N.J.) and 1% yeast extract (w/v) (Sigma, St. Louis, Mo.), which is then titrated to pH 6.0 with 5N NaOH. The culture was then shaken at 250 rpm, 30° C. for 24 hours.

The 50 mL culture was split into two 25 mL aliquots which were used as inoculum for two 1 L flasks containing MM5 medium. These flasks were shaken at 250 rpm at 30° C. for 24–48 hours. Each 1 L culture was used to inoculate 9 L of medium in Microferms (New Brunswick) for a total of 10 L volume. The Microferms were run at 30 °C.; 250 rpms to start, increasing to 450 rpms at the 24 hour point with 10 L air/minute continuous aeration.

After approximately 48 hours (average range was 36–67 hours) of growth on MM5 medium, in a 10 L stirred fermenter aerated constantly (10 L air/minute), the contents of the fermenter were harvested, and the supernatant separated from the mycelial phase by filtration/centrifugation. The activity of the fermentation broth was monitored by an Aspergillus bioassay as described below.

The cold (0° C.) supernatant phase was extracted with an equal volume of ethyl acetate (EtOAc), typically 6 L (range 6–10 L). The EtOAc extract was concentrated under vacuum at 30° C. by rotary evaporation to a tan-colored syrup of weight approximately 2.0 g (range 1.5–2.3 g).

Preparation and Separation of Compound AA02769A

The ethyl acetate extract concentrate above, was dissolved in chloroform ($CHCl_3$), typically 10 mL, and applied to a column of silica gel 60 (EM Science, Gibbstown, N.J., <230 mesh ASTM), 65 mm diameter×50 mm in height, using a step gradient ($CHCl_3$, 100; $CHCl_3$/MeOH 95:5; 92.5:7.5; 90:10; 85:15; 75:25; 50:50; 0:100; each step 200 ml volume). Fractions, 200 mL each, were collected. Fractions were monitored by TLC on Kieselgel 60 F254 (EM Separations, precoated on aluminum foil), developed with $CHCl_3$:MeOH=7:1 (v/v). The compound AA02769A appeared as a UV-absorbing band, under UV irradiation at short wavelength, at $R_f$=0.5.

A portion (about 700 mg) of the pooled fractions containing the compound AA02769A was dissolved in 60% aqueous MeOH and subjected to further chromatography, on a Lichroprep RP-18 column (EM Separations, particle size 40–63 μm). The column, packed in a 10 mL syringe, was run under vacuum and eluted with 60% (40 mL), 70% (30 mL), 80% (20 mL), and 90% (10 mL) of aqueous MeOH, and finally 100% MeOH (10 mL). The fractions were examined on RP-18 F254s TLC plates (EM Separations, Al sheets). Further purification was achieved by either silica gel column chromatography or reversed-phase preparative HPLC. Typically, a silica gel column was eluted with $CHCl_3$—MeOH with a step gradient similar to that above. Alternatively, for prep HPLC, a MeOH/$H_2O$ gradient (from 50% to 100% MeOH) was employed for elution.

The purity of the fractions was evaluated by HPLC on a C18 column (Rainin microsorb, particle size 5 μm, column size 4.6×250 mm), with a UV detector set at 240 nm. The gradient for column elution was (% MeOH in $H_2O$, minutes) : 50, 0; 100, 20; 100, 24; 50, 26. With a flow rate of 1.0 mL/min, the peak of interest has a retention time of 16.3 minutes.

Structural Characterization of Compound AA02769A

Compound AA02769A showed a $UV_{max}$ at 240 nm (ε=29,241 in MeOH), (see FIG. 3), which is typical for a conjugated diene. Electrospray (ES) IMS gave a molecular ion at m/z 415 in the negative ion mode, and a molecular ion at m/z 439 in the positive ion mode, which were in correspondence to M–H and M+Na ions, respectively, suggesting a molecular weight for the compound AA02769A of 416.

A sample of 200 mg of partially purified AA02769A (>90% pure) (from silica gel chromatography) was dissolved in pyridine, 3 ml, and acetylated. Thus, an equal volume of acetic anhydride was added to the pyridine solution, which was allowed to stand at room temperature for 15 hours. The solution was dried under vacuum at room temperature to give an acetylated derivative. This derivative was then dissolved in MeOH, 5 mL, and subjected to methylation by diazomethane, which was generated from Diazald by a standard method. The resultant reaction product was purified on a silica gel column, (40 mm diameter, 3.5 cm height). The column was run under vacuum, using elution with a step gradient of hexane-EtOAc=95:5; 90:10; 80:20; 70:30; 150 mL each step. Fractions of 150 mL were collected. Further purification of the derivative was achieved through a Lichroprep RP-18 column, eluting with a MeOH—$H_2O$ step gradient=60% to 90% MeOH. From the 80% MeOH fractions, 140 mg of pure mono-acetate, mono-methyl ester derivative of AA02769A was recovered.

Examination of the above derivative by ES/MS showed a molecular ion peak at m/z 495, corresponding to an M+Na ion of a mono-acetate, mono-methyl ester derivative of AA02769A. Thus, the molecular weight of AA02769A was confirmed as 416 (416=495–23(Na)–42(acetate)–14 (methyl)). High-resolution FAB MS of the derivative gave a mass of m/z 495.2748 for the observed ion, in accordance with a molecular formula of $C_{28}H_{40}O_6Na$ (calc. 495.2723) for this ion, and hence a molecular formula of $C_{28}H_{40}O_6$ for the derivative. Elemental analysis confirmed this composition.

The above derivative gave broad NMR peaks for several proton and carbon signals due to the fluctuation of a the ring system of the molecule. Thus, the NMR data were collected at 45° C. in $C_6D_6$. All $^1H$ NMR signals were assignable to the proposed structure for AA02769A in Scheme I (see Table 1)

TABLE 1

| $^1H$ NMR SPECTRAL PEAKS, AA02769A | |
|---|---|
| 1 | 2.23 (1H, br) |
| 2 | 2.54 (1H, br) |
| 4 | 2.72 (1H, s, $J_{4,5}$ = 0) |
| 5 | 1.74 (1H, br) |
| 6a | 1.60 (1H, dd, $J_{gem}$ = 13.5, $J_{6a,5}$ = 13.5) |
| 6e | 2.16 (1H, dd, $J_{gem}$ = 13.5, $J_{6e,5}$ = 3.0) |
| 8 | 2.95 (1H, d, $J_{8,9a}$ = 0, $J_{8,9e}$ = 5.5) |
| 9a | 1.22 (1H) |
| 9e | 1.75 (1H) |
| 10 | 1.25 (1H) |
| 11 | 1.21 (3H, s) |
| 12 | 1.35 (3H, s) |
| 1' | 5.22 (1H, dd, $J_{1',1}$ = 10.5, $J_{1',2'}$ = 14.8) |
| 2' | 6.19 (1H, br dd, $J_{1',2'}$ = 14.8, $J_{2',3'}$ = 10.8) |
| 3' | 5.96 (1H, d, $J_{3',2'}$ = 10.8) |
| 5' | 4.12 (1H, d, $J_{5',6'}$ = 9.2) |
| 6' | 2.69 (1H, dq, $J_{6',5'}$ = 9.2, $J_{6',9'}$ = 7.1) |
| 8' | 1.73 (3H, s) |
| 9' | 1.06 (3H, d, $J_{9',6'}$ = 7.1) |
| 2" | 5.22 (1H) |
| 3" | 1.64 (3H) |
| 4" | 1.65 (3H, s) |

(δppm, J in Hz, $CDCl_3$, 24° C., 500 MHz), while $^{13}C$ NMR data were assigned as shown in Table 2 (δppm, 125 MHz) to AA02769A and a methyl ester acetate derivative.

TABLE 2

| $^{13}C$ NMR SPECTRAL PEAKS, AA02769A AND A DERIVATIVE | | |
|---|---|---|
| Carbon | ($CDCl_3$, 24° C.) | ($C_6D_6$, 45° C.) |
| 1 | 43.4 | 43.9 |
| 2 | 53 (observed on HMQC) | 53.9 |

TABLE 2-continued

13C NMR SPECTRAL PEAKS, AA02769A AND A DERIVATIVE

| Carbon | (CDCl$_3$, 24° C.) | (C$_6$D$_6$, 45° C.) |
|---|---|---|
| 3 | 61 (small) | 60.4 |
| 4 | 63.2 | 62.8 |
| 5 | 33.7 | 34.2 |
| 6 | 36.1 | 36.6 |
| 7 | 58.5 | 57.5 |
| 8 | 60.0 | 59.3 |
| 9 | 29.7 | 30.9 |
| 10 | 29.3 | 33.6 (small) |
| 11 | 21.8 | 22.0 |
| 12 | 22.9 | 22.9 |
| 1' | 136.9 | 138.2 |
| 2' | 126.4 | 126.5 |
| 3' | 128.7 | 131.1 |
| 4' | 134.0 | 130.7 |
| 5' | 79.8 | 80.9 |
| 6' | 43.1 | 42.5 |
| 7' | 180.0 | 173.9 |
| 8' | 11.1 | 11.7 |
| 9' | 14.1 | 13.8 |
| 1" | 132 (observed on HMBC) | 134.1 (small) |
| 2" | 123 (observed on HMBC) | 125.0 (small) |
| 2"' | 13.6 | 13.4 |
| 4" | 21.7 (observed on HMQC) | 19 (observed on HMQC) |
| OMe |  | 51.2 |
| OAC |  | 168.7 |
|  |  | 20.4 |

EXAMPLE 2

Antifungal Assay

The anti-fungal activity of *Aspergillus fumigatus* (AA05294-Myco), was determined by an agar dilution assay on microtiter plates. A spore preparation of *Aspergillus fumigatus* was prepared by streaking out spores from a stock suspension of Aspergillus on a Subouraud Dextrose Agar (Difco) plate for germination. After 48 hours of incubation at 370+ C., the spores are washed with 0.1% Tween-80 in H$_2$O. The newly grown spores are then counted and stored at 40° C. A working spore solution of 10$^5$ spores/mL in water was used in the assay. Ser. dilutions of AA02769A were aliquoted into microtiter plates and then the plates were dried down in a vacuum centrifuge. To each well, 150 μL of Subouraud Dextrose Agar (Sab's) was added and allowed to solidify and then 10 μL of the working spore suspension was aliquoted to each well. The plates were then incubated at 35° C. for 48 hours.

General growth and sporulation were estimated as follows. The microtiter plates containing the spore suspensions were placed into a microtiter plate reader (Molecular Devices) and OD$_{650}$ readings were taken. The OD$_{650}$ readings were then analyzed by the computer program Excel (Microsoft) as follows: a value of 0 reflects 100% growth inhibition (or 0% growth); a value of 1 corresponds to 75% growth inhibition; a value of 2 corresponds to 50% growth inhibition; a value of 3 corresponds to 25% growth inhibition; a value of 4 corresponds to no growth inhibition.

Determination of antifungal activity of AA02769A against the filamentous fungi *Blastomyces dermatidis* and other fungi was determined using the same protocol as described above. Shown below are the minimum concentration of a compound that inhibits fungal growth as demonstrated by absence of fungal lawn on an agar surface (MIC μg/mL) (Table 3). Resistance of

ANTIFUNGAL ACTIVITY OF AA02769A

| ORGANISM | MYCO# | MIC (μg/mL) |
|---|---|---|
| Aspergillus fumigatus | H237 | 62.5 |
| Aspergillus fumigatus | AA11101 (RCan1) | 62.5 |
| Aspergillus fumigatus | AA11102 (AHar3) | 62.5 |
| Aspergillus fumigatus | AA11103 (PLaf1) | 125 |
| Aspergillus fumigatus | AA11104 (JWil1) | 125 |
| Aspergillus fumigatus | AA11104 (JWil1) | 125 |
| Aspergillus fumigatus | AA11105 (BDup1) | 125 |
| Aspergillus fumigatus | AA11105 (FRos1) | 125 |
| Aserqillus flavus | AA03382 | 250 |
| Aspergillus nidulans | AA02337 | 15.5 |
| Blastomyces dermatidis | AA011108 | 62.5 |
| Candida albicans | ATCC10261 | >500 |
| Candida albicans | ATCC90028 | >500 |
| Candida albicans | ATCC90029 | >500 |
| Cryptoccccus neoformans | ATCC90112 | >500 |
| Cryptococcus neoformans | ATCC90113 | >500 |
| Fusarium solani | AA11100 | >500 |
| Geotrichum candidum | AA00447 | >500 |
| Penicillium grisecfulvin | AA06797 | >500 |

*A. fumigatus* to AA02769A was determined as follows. An AA02769A-containing extract in 100% methanol; 0.1 mL (plate a), 0.05 mL (plate b), and 0.025 mL (plate c) of the extract (~10 mg/mL) was placed into 60 cm petri plates and the methanol was allowed to evaporate from each plate. To each plate, 10 mL of molten (50 OC) SDA medium (Soubaraud-Dextrose+2% (w/v) Bacto Agar) were added, mixed by swirling, and allowed to cool for 3 hours. The plates were then inoculated with 0.015 mL of 105 spores/mL of *A. fumigatus* (strain AA05294-Myco) and incubated at 35° C. After incubation, plates a and b showed very little growth. Plate c showed what appeared to be a fast growing sector. An isolate was taken from this region and tested against AA02769A in SDA medium as described above with 0.2 mL (plate a), 0.1 mL (plate b), 0.05 mL (plate c). Growth after 11 days showed no fast growing sectors in the isolate from plate c or controls from the original spore stock. No evidence was found for spontaneous resistance in these growing cultures representing production of millions of nuclei over the eleven day period. These results show that AA02769A inhibits growth of *A. fumigatus* at concentrations between 240 mM and 120 mM.

EXAMPLE 3

Derivatization of Compound AA02769A

AA02769A can be derivatized to compounds AA02769C, D, and E (Scheme I, above) by standard chemical methods. For example, to synthesize AA02769C, compound AA02769A is treated with an acid such as p-toluenesulfonic acid. To synthesize AA02769D, compound AA02769A is simply treated with 1N HCl. Compound AA02769E is synthesized by simple substitution of the less hindered C-7,8 epoxide of compound AA02769A by the carboxyl group of additional compound AA02769A. Synthesis of more complicated derivatives is discussed above.

Other Embodiments

From the above description, the essential characteristics of the present invention can be easily ascertained. Without departing from the spirit and scope thereof, various changes and modifications of the invention can be made to adapt it to various usages and conditions. Thus, other embodiments are also within the claims.

What is claimed is:

1. A compound having the formula:

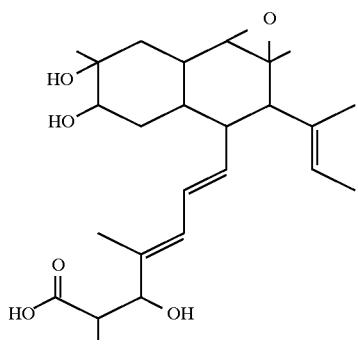

or a pharmaceutically acceptable salt thereof.

2. A compound having the formula:

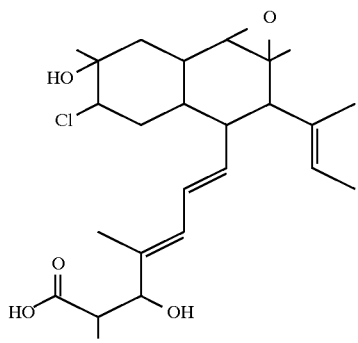

or a pharmaceutically acceptable salt thereof.

3. A compound having the formula:

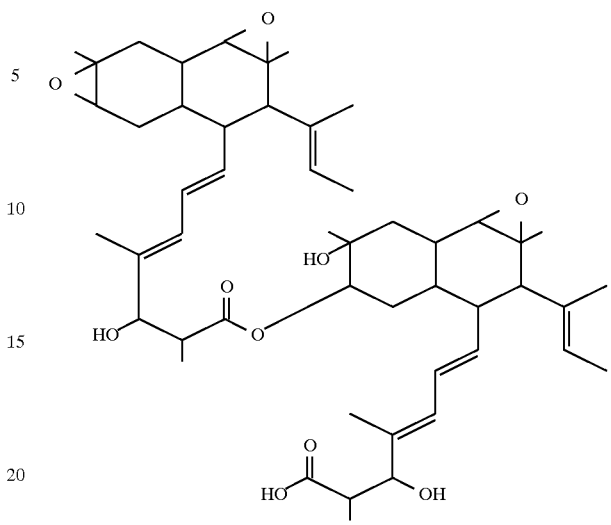

or a pharmaceutically acceptable salt thereof.

4. A method for treating mycotic infections in an organism, which comprises administering to an organism in need of such treatment, a therapeutically effective amount of the compound of claim 1, in a pharmaceutically acceptable vehicle, thereby inhibiting a mycotic infection in the organism.

5. A method for treating mycotic infections in an organism, which comprises administering to an organism in need of such treatment a therapeutically effective amount of the compound of claim 2, in a pharmaceutically acceptable vehicle, thereby inhibiting a mycotic infection in the organism.

6. A method for treating mycotic infections in an organism, which comprises administering to an organism in need of such treatment a therapeutically effective amount of the compound of claim 3, in a pharmaceutically acceptable vehicle, thereby inhibiting a mycotic infection in the organism.

* * * * *